US008685708B2

(12) United States Patent
Harris et al.

(10) Patent No.: US 8,685,708 B2
(45) Date of Patent: Apr. 1, 2014

(54) DEVICE FOR PREPARING A SAMPLE (71) Applicant: PathoGenetix, Inc., Woburn, MA (US)

(72) Inventors: John L. Harris, Foxboro, MA (US); Adrian Mark Thomas West, Newton, MA (US); Dirk Peter Ten Broeck, Nashua, NH (US); Ekaterina Protozanova, Arlington, MA (US)

(73) Assignee: PathoGenetix, Inc., Woburn, MA (US)

( * ) Notice: Subject to any disclaimer, the term of this patent is extended or adjusted under 35 U.S.C. 154(b) by 0 days.

(21) Appl. No.: 13/862,081

(22) Filed: Apr. 12, 2013

(65) Prior Publication Data

US 2013/0288234 A1 Oct. 31, 2013

Related U.S. Application Data (60) Provisional application No. 61/625,743, filed on Apr. 18, 2012, provisional application No. 61/783,601, filed on Mar. 14, 2013.

(51) Int. Cl.
| C12M 1/00 | (2006.01) |
|---|---|
| C12Q 1/68 | (2006.01) |
| C12M 1/34 | (2006.01) |
| C12M 1/12 | (2006.01) |
| B01D 61/00 | (2006.01) |
| C02F 1/44 | (2006.01) |

(52) U.S. Cl.
USPC ... 435/283.1; 435/6.1; 435/288.2; 435/288.5; 435/295.3; 210/650

(58) Field of Classification Search
USPC .............. 435/6.1, 283.1, 288.2, 288.5, 295.3; 210/650
See application file for complete search history.

(56) References Cited

U.S. PATENT DOCUMENTS

| 3,954,621 A | 5/1976 | Etani et al. |
|---|---|---|
| 3,969,218 A | 7/1976 | Scott |
| 4,147,621 A | 4/1979 | Giddings |
| 4,545,888 A | 10/1985 | Walsh |
| 4,608,147 A | 8/1986 | Clad et al. |
| 4,617,102 A | 10/1986 | Tomblin et al. |
| 4,833,332 A | 5/1989 | Robertson, Jr. et al. |
| 4,964,961 A | 10/1990 | Brautigam et al. |
| 5,102,518 A | 4/1992 | Doering et al. |
| 5,126,022 A | 6/1992 | Soane et al. |
| 5,133,844 A | 7/1992 | Stevens |
| 5,141,651 A | 8/1992 | Giddings |
| 5,169,511 A | 12/1992 | Allington et al. |
| 5,284,559 A | 2/1994 | Lim et al. |
| 5,304,487 A | 4/1994 | Wilding et al. |
| 5,318,680 A | 6/1994 | Fishman et al. |
| 5,340,449 A | 8/1994 | Shukla |
| 5,427,663 A | 6/1995 | Austin et al. |
| 5,439,573 A | 8/1995 | Luo |
| 5,449,917 A | 9/1995 | Clements |
| 5,453,382 A | 9/1995 | Novotny et al. |
| 5,505,831 A | 4/1996 | Liao et al. |
| 5,601,694 A | 2/1997 | Maley et al. |
| 5,674,743 A | 10/1997 | Ulmer |
| 5,675,155 A | 10/1997 | Pentoney, Jr. et al. |
| 5,699,157 A | 12/1997 | Parce |
| 5,711,861 A | 1/1998 | Ward et al. |
| 5,711,868 A | 1/1998 | Maley et al. |
| 5,733,442 A | 3/1998 | Shukla |
| 5,766,435 A | 6/1998 | Liao et al. |
| 5,798,215 A | 8/1998 | Cathey et al. |
| 5,800,690 A | 9/1998 | Chow et al. |
| 5,837,115 A | 11/1998 | Austin et al. |
| 5,843,767 A | 12/1998 | Beattie |
| 5,846,727 A | 12/1998 | Soper et al. |
| 5,867,266 A | 2/1999 | Craighead |
| 5,879,625 A | 3/1999 | Roslaniec et al. |
| 5,880,473 A | 3/1999 | Ginestet |
| 5,888,370 A | 3/1999 | Becker et al. |
| 5,906,723 A | 5/1999 | Mathies et al. |
| 5,942,093 A | 8/1999 | Rakestraw et al. |
| 5,965,001 A | 10/1999 | Chow et al. |
| 5,971,158 A | 10/1999 | Yager et al. |
| 6,001,229 A | 12/1999 | Ramsey |
| 6,008,892 A | 12/1999 | Kain et al. |
| 6,013,164 A | 1/2000 | Paul et al. |
| 6,019,882 A | 2/2000 | Paul et al. |
| 6,071,394 A | 6/2000 | Cheng et al. |
| 6,071,395 A | 6/2000 | Lange |
| 6,090,251 A | 7/2000 | Sundberg et al. |
| 6,100,541 A | 8/2000 | Nagle et al. |

(Continued)

FOREIGN PATENT DOCUMENTS

| EP | 1 380 337 A2 | 1/2004 |
|---|---|---|
| GB | 2148325 | 5/1985 |

(Continued)

OTHER PUBLICATIONS

Burton et al., A microfluidic chip-compatible bioassay based on single-molecule detection with high sensitivity and multiplexing. Lab Chip. Apr. 7, 2010;10(7):843-51. Epub Jan. 14, 2010.

(Continued)

*Primary Examiner* — Narayan Bhat
(74) *Attorney, Agent, or Firm* — Wolf, Greenfield & Sacks, P.C.

(57) ABSTRACT

The invention provides a device for preparing a fluid sample, including but not limited to a sample comprising genomic DNA.

11 Claims, 8 Drawing Sheets

(56) References Cited

U.S. PATENT DOCUMENTS

| | | | |
|---|---|---|---|
| 6,120,666 A | 9/2000 | Jacobson et al. |
| 6,139,800 A | 10/2000 | Chandler |
| 6,193,647 B1 | 2/2001 | Beebe et al. |
| 6,210,896 B1 | 4/2001 | Chan |
| 6,214,246 B1 | 4/2001 | Craighead |
| 6,218,126 B1 | 4/2001 | Yasuda et al. |
| 6,224,728 B1 | 5/2001 | Oborny et al. |
| 6,232,464 B1 | 5/2001 | Lange |
| 6,263,286 B1 | 7/2001 | Gilmanshin et al. |
| 6,277,257 B1 | 8/2001 | Paul et al. |
| 6,319,469 B1 | 11/2001 | Mian et al. |
| 6,319,472 B1 | 11/2001 | Ackley et al. |
| 6,355,420 B1 | 3/2002 | Chan |
| 6,403,311 B1 | 6/2002 | Chan |
| 6,413,401 B1 | 7/2002 | Chow et al. |
| 6,428,666 B1 | 8/2002 | Singh et al. |
| 6,432,630 B1 | 8/2002 | Blankenstein |
| 6,444,992 B1 | 9/2002 | Kauvar et al. |
| 6,489,112 B1 | 12/2002 | Hadd et al. |
| 6,495,015 B1 | 12/2002 | Schoeniger et al. |
| 6,506,609 B1 | 1/2003 | Wada et al. |
| 6,562,307 B1 | 5/2003 | Schuch et al. |
| 6,572,749 B1 | 6/2003 | Paul et al. |
| 6,605,454 B2 | 8/2003 | Barenburg et al. |
| 6,641,708 B1 | 11/2003 | Huang et al. |
| 6,645,757 B1 | 11/2003 | Okandan et al. |
| 6,660,480 B2 | 12/2003 | Ramsey et al. |
| 6,696,022 B1 | 2/2004 | Chan et al. |
| 6,762,059 B2 | 7/2004 | Chan et al. |
| 6,767,731 B2 | 7/2004 | Hannah et al. |
| 6,770,182 B1 | 8/2004 | Griffiths et al. |
| 6,770,201 B2 | 8/2004 | Shepodd et al. |
| 6,772,070 B2 | 8/2004 | Gilmanshin et al. |
| 6,790,671 B1 | 9/2004 | Austin et al. |
| 6,818,113 B2 | 11/2004 | Williams et al. |
| 6,866,759 B2 | 3/2005 | Miles et al. |
| 6,890,411 B1 | 5/2005 | Hayes et al. |
| 6,914,137 B2 | 7/2005 | Baker |
| 6,927,065 B2 | 8/2005 | Chan et al. |
| 6,943,009 B2 | 9/2005 | Lacey et al. |
| 6,949,355 B2 * | 9/2005 | Yamanishi et al. ............ 435/34 |
| 6,960,285 B2 | 11/2005 | Schoeniger et al. |
| 6,998,598 B2 | 2/2006 | Horn et al. |
| 7,014,747 B2 | 3/2006 | Cummings et al. |
| 7,052,608 B2 | 5/2006 | Shepodd et al. |
| 7,094,345 B2 | 8/2006 | Gilbert et al. |
| 7,262,859 B2 | 8/2007 | Larson et al. |
| 7,282,330 B2 | 10/2007 | Zhao et al. |
| 7,332,126 B2 | 2/2008 | Tooke et al. |
| 7,351,538 B2 | 4/2008 | Fuchs et al. |
| 7,371,520 B2 | 5/2008 | Zhao et al. |
| 7,402,422 B2 | 7/2008 | Fuchs et al. |
| 7,595,160 B2 | 9/2009 | White et al. |
| 7,648,677 B2 | 1/2010 | Santini, Jr. et al. |
| 7,828,948 B1 | 11/2010 | Hatch et al. |
| 7,888,011 B2 | 2/2011 | Nilsen et al. |
| 7,977,048 B2 | 7/2011 | Gilmanshin |
| 8,114,636 B2 | 2/2012 | Agnew et al. |
| 8,168,380 B2 | 5/2012 | Chan |
| 8,361,716 B2 | 1/2013 | Patil |
| 8,423,294 B2 | 4/2013 | Nadel et al. |
| 2001/0030130 A1 | 10/2001 | Ricco et al. |
| 2001/0055817 A1 | 12/2001 | Malmqvist et al. |
| 2002/0008028 A1 | 1/2002 | Jacobson et al. |
| 2002/0029814 A1 | 3/2002 | Unger et al. |
| 2002/0034748 A1 | 3/2002 | Quake et al. |
| 2002/0055167 A1 | 5/2002 | Pourahmadi et al. |
| 2002/0058332 A1 | 5/2002 | Quake et al. |
| 2002/0072243 A1 | 6/2002 | Craighead et al. |
| 2002/0079008 A1 | 6/2002 | Chien et al. |
| 2002/0109844 A1 | 8/2002 | Christel et al. |
| 2002/0110495 A1 | 8/2002 | Hunt et al. |
| 2002/0110818 A1 | 8/2002 | Chan |
| 2002/0119455 A1 | 8/2002 | Chan |
| 2002/0187508 A1 | 12/2002 | Wong |
| 2002/0197639 A1 | 12/2002 | Shia et al. |
| 2003/0008320 A1 | 1/2003 | Baker |
| 2003/0010637 A1 | 1/2003 | Cummings |
| 2003/0054395 A1 | 3/2003 | Baker |
| 2003/0058440 A1 | 3/2003 | Scott et al. |
| 2003/0059822 A1 | 3/2003 | Chan et al. |
| 2003/0104466 A1 | 6/2003 | Knapp et al. |
| 2003/0124623 A1 | 7/2003 | Yager et al. |
| 2003/0130499 A1 | 7/2003 | Baker |
| 2003/0134416 A1 | 7/2003 | Yamanishi et al. |
| 2003/0162181 A1 | 8/2003 | Yang et al. |
| 2003/0215864 A1 | 11/2003 | Gilmanshin et al. |
| 2003/0235854 A1 | 12/2003 | Chan et al. |
| 2004/0000519 A1 | 1/2004 | Jiang et al. |
| 2004/0028580 A1 | 2/2004 | Futami et al. |
| 2004/0053399 A1 | 3/2004 | Gilmanshin |
| 2004/0084370 A1 | 5/2004 | Singh et al. |
| 2004/0126279 A1 | 7/2004 | Renzi et al. |
| 2004/0166025 A1 | 8/2004 | Chan et al. |
| 2004/0188254 A1 | 9/2004 | Spaid |
| 2004/0211669 A1 | 10/2004 | Cummings et al. |
| 2004/0214211 A1 | 10/2004 | Gilmanshin et al. |
| 2004/0235014 A1 | 11/2004 | Nadel et al. |
| 2005/0009066 A1 | 1/2005 | Connolly |
| 2005/0042665 A1 | 2/2005 | Gilmanshin et al. |
| 2005/0112606 A1 | 5/2005 | Fuchs et al. |
| 2005/0112620 A1 | 5/2005 | Chan |
| 2005/0112671 A1 | 5/2005 | Maletta et al. |
| 2005/0123944 A1 | 6/2005 | Neely et al. |
| 2005/0123974 A1 | 6/2005 | Gilmanshin et al. |
| 2005/0142565 A1 | 6/2005 | Samper et al. |
| 2005/0142595 A1 | 6/2005 | Maletta et al. |
| 2005/0148064 A1 | 7/2005 | Yamakawa et al. |
| 2005/0153354 A1 | 7/2005 | Gilmanshin |
| 2005/0191760 A1 | 9/2005 | Heath et al. |
| 2005/0196790 A1 | 9/2005 | Rooke |
| 2005/0221408 A1 | 10/2005 | Nalefski et al. |
| 2006/0134679 A1 | 6/2006 | Larson |
| 2006/0160231 A1 | 7/2006 | Nadel et al. |
| 2006/0191792 A1 | 8/2006 | Herr et al. |
| 2006/0194306 A1 | 8/2006 | Herr et al. |
| 2006/0204978 A1 | 9/2006 | Nilsen et al. |
| 2006/0211055 A1 | 9/2006 | Hafeman et al. |
| 2006/0292616 A1 | 12/2006 | Neely et al. |
| 2006/0292617 A1 | 12/2006 | Neely et al. |
| 2007/0031961 A1 | 2/2007 | Ho et al. |
| 2007/0042406 A1 | 2/2007 | Yantz et al. |
| 2007/0117092 A1 | 5/2007 | Sadarangani et al. |
| 2007/0128083 A1 | 6/2007 | Yantz et al. |
| 2007/0166743 A1 | 7/2007 | Gilmanshin |
| 2008/0003689 A1 | 1/2008 | Lee et al. |
| 2008/0085552 A1 | 4/2008 | Larson et al. |
| 2008/0103296 A1 | 5/2008 | Zhao et al. |
| 2008/0254549 A1 | 10/2008 | Fuchs et al. |
| 2008/0280285 A1 | 11/2008 | Chen et al. |
| 2009/0035770 A1 | 2/2009 | Mathies et al. |
| 2009/0325269 A1 * | 12/2009 | Marschke ............... 435/235.1 |
| 2010/0035247 A1 | 2/2010 | Burton et al. |
| 2010/0112576 A1 * | 5/2010 | Patil ............... 435/6 |
| 2010/0116025 A1 | 5/2010 | Gouveia et al. |
| 2010/0120101 A1 | 5/2010 | Patil et al. |
| 2010/0234237 A1 | 9/2010 | Yoo |
| 2010/0294665 A1 | 11/2010 | Allen et al. |
| 2012/0283955 A1 | 11/2012 | Cameron et al. |
| 2013/0000738 A1 | 1/2013 | Krogmeier et al. |
| 2013/0266935 A1 | 10/2013 | Patil |
| 2013/0295686 A1 | 11/2013 | Meltzer et al. |
| 2013/0309780 A1 | 11/2013 | Meltzer et al. |

FOREIGN PATENT DOCUMENTS

| | | |
|---|---|---|
| JP | 63-196845 A | 8/1988 |
| JP | 3075602 | 3/1991 |
| JP | 5072178 | 3/1993 |
| JP | 5223778 | 8/1993 |
| JP | 8327595 | 12/1996 |
| JP | 2005-181204 | 7/2005 |
| WO | WO 94/16313 A2 | 7/1994 |
| WO | WO 98/30571 A1 | 7/1998 |

(56) References Cited

FOREIGN PATENT DOCUMENTS

| | | |
|---|---|---|
| WO | WO 98/35012 A2 | 8/1998 |
| WO | WO 99/09042 A2 | 2/1999 |
| WO | WO 00/09757 A1 | 2/2000 |
| WO | WO 00/50172 A1 | 8/2000 |
| WO | WO 00/56444 A2 | 9/2000 |
| WO | WO 00/70080 A1 | 11/2000 |
| WO | WO 01/28700 A1 | 4/2001 |
| WO | WO 02/29106 A2 | 4/2002 |
| WO | WO 03/000416 A2 | 1/2003 |
| WO | WO 2004/076692 A1 | 9/2004 |
| WO | WO 2005/078137 A1 | 8/2005 |
| WO | WO 2005/085849 A2 | 9/2005 |
| WO | WO 2006/017274 A2 | 2/2006 |
| WO | WO 2008/024483 A1 | 2/2008 |
| WO | WO 2008/085991 A2 | 7/2008 |
| WO | WO 2008/111959 A2 | 9/2008 |
| WO | WO 2009/009127 A2 | 1/2009 |
| WO | WO 2010/149292 A1 | 12/2010 |
| WO | WO 2011/102804 A1 | 8/2011 |

OTHER PUBLICATIONS

Mollova et al., An automated sample preparation system with mini-reactor to isolate and process submegabase fragments of bacterial DNA. Anal Biochem. Aug. 15, 2009;391(2):135-43. Epub May 12, 2009. Supplemental Material Included. 23 pgs.

Protozanova et al., Fast high-resolution mapping of long fragments of genomic DNA based on single-molecule detection. Anal Biochem. Jul. 1, 2010;402(1):83-90. Epub Mar. 20, 2010. Supplemental Material Included. 29 pgs.

[No Author Listed] Figure 5. Physics Today Online. Available at http://www.physicstoday.org/pt/vol-54/iss-6/captions/p42cap5.html. Last accessed Jul. 15, 2002. 2 pages.

[No Author Listed] FRAEN FLP Series Lenses for Luxeon LEDs: Luxeon I, III, and V, Star and Emitter. Jan. 4, 2005. Available at http://www.fraensrl.com/images/FLP_Lens_Series_Datasheet.pdf. 8 pages.

Agronskaia et al. Two-color fluorescence in flow cytometry DNA sizing: Identification of single-molecule fluorescent probes. Anal. Chem. 1999;71:4684-4689. Abstract.

Ashworth. et al., Transducer mechanisms for optical biosensors. Part 2: Transducer design. Comput Methods Programs Biomed. Sep. 1989;30(1):21-31.

Bender et al., Surveillance for *Escherichia coli* O157:H7 infections in Minnesota by molecular subtyping. N Engl J Med. Aug. 7, 1997;337(6):388-94.

Boone et al., Plastic advances microfluidic devices. Anal Chem. Feb. 1, 2000;74(3):78A-86A.

Burns et al., An integrated nanoliter DNA analysis device. Science. Oct. 16, 1998;282(5388):484-7.

Chan et al., DNA mapping technology based on microfluidic stretching and single-molecule detection of motif tags. Biophys J. 2003;84:302A. Poster 1470. Board #B725.

Chan et al., DNA mapping using microfluidic stretching and single-molecule detection of fluorescent site-specific tags. Genome Res. Jun. 2004;14(6):1137-46.

Cheek et al., Chemiluminescence detection for hybridization assays on the flow-thru chip, a three-dimensional microchannel biochip. Anal Chem. Dec. 15, 2001;73(24):5777-83.

Chou et al., A microfabricated device for sizing and sorting DNA molecules. Proc Natl Acad Sci U S A. Jan. 5, 1999;96(1):11-13.

Cova et al., Evolution and prospects for single-photon avalanche diodes and quenching circuits. J Mod Opt. Jun.-Jul. 2004;51(9-10):1267-88.

D'Antoni et al., Single Molecule Detection of Proteins Using Microfluidic Fluorescence Detection. ORC Poster. Apr. 2006. 1 page.

Dittrich et al., Sorting of cells and single particles in microstructures. Biophys J. 2002;82:43a. 209-Pos. Board # B70.

Duke et al., Microfabricated sieve for the continuous sorting of macromolecules. Phys. Rev. Lett. 1998; 80:1552-1555. Abstract Only.

Ertas, Lateral separation of macromolecules and polyelectrolytes in microlithographic arrays. Phys. Rev. Lett. 1998; 80:1548-1551. Abstract Only.

Foquet et al., DNA fragment sizing by single molecule detection in submicrometer-sized closed fluidic channels. Anal Chem. Mar. 15, 2002;74(6):1415-22. (Abstract Only).

Giddings et al., Chapter 1. The Field-Flow Fractionation Family: Underlying Principles. In: Field-Flow Fractionation Handbook. Wiley-Interscience. 2000: 3-30.

Han et al., Separation of long DNA molecules in a microfabricated entropic trap array. Science. May 12, 2000;288(5468):1026-9.

Harrison et al., Capillary Electrophoresis and Sample Injection Systems Integrated on a Planar Glass Chip, Anal. Chem. 1992; 64:1926.

Jacobson et al., Fused Quartz Substrates for Microchip Electrophoresis. Anal Chem. 1995; 67:2059. Abstract Only.

Krogmeier et al., A Microfluidic Device for Concentrating High Molecular Weight DNA. Mar. 2, 2009; 315a. 1608 Pos. Board B452. Abstract Only.

Kumar et al., Evaluation of genome sequence scanning technology for molecular (sub)-serotyping of *Salmonella* and simultaneous detection of multiple *Salmonella* serovars in complex mixtures. 4th Am Soc for Microbiol (ASM) Meeting on *Salmonella*. Oct. 9, 2013. Poster. 1 Page.

Kumar et al., Molecular serotyping and sub-typing of *Salmonella* strains by genome sequence scanning. Int'l Assoc for Food Protect Ann Mtg. Jul. 31, 2013. Poster. 1 Page.

Kumar et al., Molecular strain typing of Shiga-toxigenic *E. coli* (STEC) by genome sequence scanning. Assoc Pub Health Lab Gen Mtg. Jun. 2, 2013. 1 Page.

Kumar et al., Molecular strain typing of Shiga-toxigenic *E. coli* (STEC) by genome sequence scanning. Am Soc for Microbiol Gen mtg. May 20, 2013. Poster. 1 Page.

Kwok et al., An Integrated Multifunction Lab-on-a-Chip Platform for Hugh Throughput Optical Mapping for DNA. Nanotechnology. 2009;48a. 244-Pos. Board B123. Abstract Only.

Kwok et al., An Integrated Multifunction Lab-on-a-Chip Platform for Hugh Throughput Optical Mapping for DNA. Biophysical Society 53rd Annual Meeting. Feb. 28-Mar. 4, 2009. Boston. Poster. 1 Page.

Larson et al., Single DNA molecule stretching in sudden mixed shear and elongational microflows. Lab Chip. 2006;6(9):1187-1199.

Lee et al., Analysis of self-assembled cationic lipid-DNA gene carrier complexes using flow field-flow fractionation and light scattering. Anal Chem. Feb. 15, 2001;73(4):837-43.

Lee et al., Micro flow cytometers with buried SU-8/SOG optical waveguides. Sensors and Actuators. 2003;103:165-70.

Lee et al., Mircomachined pre-focused M×N flow switches for continuous multi-sample injection, J Micromech Microeng. 2001;11:654-661.

Li et al., Chapter 28. Protein Complexes and Lipoproteins. In: Field Flow Fractionation Handbook. Wiley-Interscience. 2000: 433-470.

Liu et al., Separation and Measurement of Diffusion Coefficients of Linear and Circular DNAs by Flow Field-Flow Fractionation. Macromolecules. 1993; 26(14):3576-88.

Lyon et al., 1997, "Confinement and detection of single molecules in submicrometer channels", Anal. Chem. 69:3400-3405. Abstract.

Malkin et al., Rapid detection and sub-serotype level typing of bacterial organisms using optical genome sequence scanning. Am Soc Microbiol Gen Meeting. 2013. Poster. 1 Page.

Meltzer et al., A lab-on-chip for biothreat detection using single-molecule DNA mapping. Lab Chip. Mar. 7, 2011;11(5):863-73. Epub Jan. 20, 2011. Supplemental Material Included. 16 Pages.

Nie et al., Probing individual molecules with confocal fluorescence microscopy. Science. Nov. 11, 1994;266(5187):1018-21.

Noller et al., Multilocus sequence typing reveals a lack of diversity among *Escherichia coli* O157:H7 isolates that are distinct by pulsed-field gel electrophoresis. J Clin Microbiol. Feb. 2003;41(2): 675-9.

Papkov et al., A single-molecule system for detection and quantification of proteins with robust capture units and potential for high multiplexing. Biophysical Society 53rd Annual Meeting. Feb. 28-Mar. 4, 2009. Boston. Poster. 10 Pages.

Pasquinelli et al., Control of developmental timing by micrornas and their targets. Annu Rev Cell Dev Biol. 2002;18:495-513. Epub Apr. 2, 2002. Abstract.

(56) References Cited

OTHER PUBLICATIONS

Phillips et al., Application of single molecule technology to rapidly map long DNA and study the confirmation of stretched DNA. Nuc Acids Res. 2005;33(18):5829-5837.

Pouseele et al., An Integrated Rapid Strain Typing Solution Combined With a Polyphasic Bioinformatics Tool has the Potential to Considerably Reduce the Time for Routine Outbreak Detection. InFORM 2013: Integrated Foodborne Outbreak Response and Management Meeting. Nov. 19, 2013. Poster. 1 Page.

Protozanova et al., Binding Specificity of Multi-Labeled PNA Probes Studied by Single Molecule Mapping. Biophysical Society 53rd Annual Meeting. Feb. 28-Mar. 4, 2009. Boston. 25a. 124-Pos. Board B3. Abstract.

Radcliff et al., Chapter 1. Basics of flow cytometry. In: Methods Mol Biol. 1998;91:1-24.

Ramaswamy et al., Confirmation and typing of *Salmonella* by genome sequence scanning in preseumptive positive food samples. Pathogenex Poster. Jul. 30, 2013. 1 Page.

Ramaswamy et al., Rapid strain typing of *Salmonella* in food in the presence of competing microflora by genome sequence scanning. Am Soc Microbiol Gen Mtg. May 29, 2013. Poster. 1 Page.

Roulet et al., Fabrication of multilayer systems combining microfluidic and microoptical elements for fluorescence detection. J Micro Systems. Dec. 2001;10(4):482-91.

Roulet et al., Performance of an integrated microoptical system for fluorescence detection in microfluidic systems. Anal Chem. Jul. 15, 2002;74(14):3400-7.

Schmalzing et al., 1997, "DNA typing in thirty seconds with a microfabricated device", Proc. Natl. Acad. Sci. USA 94:10273-10278.

Schmalzing et al., 1998, "DNA sequencing on microfabricated electrophoretic devices", Anal. Chem. 70:2303-2310. Abstract Only.

Shera et al., Detection of single fluorescent molecules. Chem Phys Letts. Nov. 23, 1990;174(6):553-7.

Soper et al., Nanoliter-scale sample preparation methods directly coupled to polymethylmethacrylate-based microchips and gel-filled capillaries for the analysis of oligonucleotides. J Chromatography A. 1999;853:107-20.

Wabuyele et al., Single molecule detection of double-stranded DNA in poly(methylmethacrylate) and polycarbonate microfluidic devices. Electrophoresis. Oct. 2001;22(18):3939-48. (Abstract Only).

Wahlund et al., Application of an asymmetrical flow field-flow fractionation channel to the separation and characterization of proteins, plasmids, plasmid fragments, polysaccharides and unicellular algae. J Chromatogr. Jan. 6, 1989;461:73-87.

Washizu et al., 1990, "Electrostatic manipulation of DNA in microfabricated structures", IEEE Trans Industry Applications 26:1165-1172. Abstract.

Watson et al., The early fluidic and optical physics of cytometry. Cytometry. Feb. 15, 1999;38(1):2-14.

White et al., *Staphylococcus aureus* strain typing by single-molecule DNA mapping in fluidic microchips with fluorescent tags. Clin Chem. Dec. 2009;55(12):2121-9. Epub Oct. 8, 2009.

White et al., *Staphylococcus aureus* strain typing by single-molecule DNA mapping in fluidic microchips with fluorescent tags. Clin Chem. Dec. 2009;55(12):2121-9. Epub 2009 Oct. 8. Supplemental Data. 22 Pages.

Whitesides et al., Flexible Methods for Microfluidics: Devices for handling nanoliter qualities of fluids are creating new fabrication challenges and finding new applications in biology, chemistry, and materials science. Physics Today Online. Jun. 2001, 8 pages.

Whitesides et al., Generating Microgradients. Harvard MRSEC—Research Nuggets. Materials Research Science and Engineering Center. Feb. 2, 2001. Available at http://www.mrsec.harvard.edu/research/nugget_4.html. Last accessed Jul. 15, 2002. 1 page.

Whitesides, Fabrication of Complex, 3D Microstructures. Harvard MRSEC—Research Nuggets. Materials Research Science and Engineering Center. Available at http://www.mrsec.harvard.edu/research/nugget_3.html. Last accessed Jul. 15, 2002. 1 page.

Whitesides, Three-Dimensional Networks of Fluid Channels in PDMS. Harvard MRSEC—Research Nuggets. Materials Research Science and Engineering Center. Jun. 1, 2000. Available at http://www.mrsec.harvard.edu/research/nugget_11.html. Last accessed Jul. 15, 2002. 1 page.

Wilding, et al Manipulation and flow of biological fluids in straight channels micromachined in silicon. Clin. Chem. 1994, vol. 40, No. 1, pp. 43-47.

Wong et al., 2002, "Direct Manipulations of DNA Molecules Using Hydrodynamic Force", 2002 IEEE International Conference on Robotics and Automation, Washington D.C. 27 Pages.

\* cited by examiner

FIG. 7

DEVICE FOR PREPARING A SAMPLE

RELATED APPLICATIONS

This application claims the benefit under 35 U.S.C. §119 (e) of U.S. Provisional Application Ser. No. 61/625,743, entitled "DEVICE FOR PREPARING A SAMPLE" filed on Apr. 18, 2012, and U.S. Provisional Application Ser. No. 61/783,601, entitled "DEVICE FOR PREPARING A SAMPLE" filed on Mar. 14, 2013, the entire contents of both of which are incorporated herein by reference.

FIELD OF INVENTION

The present invention is directed to a device for preparing a fluid sample, including but not limited to samples which include genomic DNA. More particularly, aspects of the present invention are directed to a device with a reaction chamber and a porous membrane.

SUMMARY OF INVENTION

According to one aspect, a device for preparing a sample is provided. The device includes a body having a chamber with an inlet and a membrane positioned in the body. The membrane has a first side and a second side, where the inlet is positioned on the first side of the membrane. The device also includes a plurality of channels optionally coupled to the bottom of the chamber, where the plurality of channels are optionally positioned on the second side of the membrane. Each of the plurality of channels extends outwardly from the membrane, the plurality of channels including at least a first channel and a second channel, where the first channel extends outwardly from a central portion of the membrane, and where the second channel extends outwardly from a peripheral portion of the membrane.

According to another aspect, a device for preparing a sample is provided. The device includes a body having a chamber with an inlet and a membrane positioned in the body. The membrane has a first side and a second side, where the inlet is positioned on the first side of the membrane. The membrane includes at least a first zone and a second zone, where the first zone is the central portion of the membrane and the second zone is the peripheral portion of the membrane and there is a barrier which separates the first zone of the membrane from the second zone of the membrane. The device also includes a plurality of channels coupled to the bottom of the chamber, where the plurality of channels are positioned on the second side of the membrane, in some embodiments.

The present invention further encompasses methods of making and/or using one or more of the embodiments described herein.

Other advantages and novel features of the present invention will become apparent from the following detailed description of various non-limiting embodiments of the invention when considered in conjunction with the accompanying Figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

Non-limiting embodiments of the present invention will be described by way of example with reference to the accompanying Figures, which are schematic and are not intended to be drawn to scale. For purposes of clarity, not every component is labeled in every figure, nor is every component of each embodiment of the invention shown where illustration is not necessary to allow those of ordinary skill in the art to understand the invention.

DETAILED DESCRIPTION OF INVENTION

The invention in its broadest sense provides devices and methods of use thereof for positioning or manipulating or concentrating agents within a fluid, including but not limited to polymers such as genomic DNA. Aspects of the invention allow the agents to be concentrated into relatively small portions of the fluid. This may provide a higher concentration of the agent within a portion of the fluid, or decrease losses as the agent undergoes processing due to a decrease of contact area between the agent and the membrane.

Certain aspects of the invention relate to using a chamber for positioning or manipulating an agent, such as genomic DNA. In some aspects, the chamber is minimally comprised of an inlet port, a porous membrane that allows fluid but not the agent of interest to pass through, and a plurality of channels positioned on a side of the porous membrane opposite the inlet port. The chamber may be operated in a first mode where a fluid containing agents is introduced into the chamber through the inlet port and flowed through the porous membrane in the chamber. Fluid may be introduced through one or more of the channels to move a portion of the fluid towards a peripheral portion of the membrane. The desired agents may then be positioned on the central portion of the membrane. Flow may be reversed through the inlet port to move any agents positioned on the membrane out of the chamber in central streamlines that exit the chamber through the first fluid port.

The invention is based in part on devices with chambers (referred to herein interchangeably as a "reaction chamber" or a "fluidic chamber") that may be used to concentrate a fluid sample, which may contain various agents, to a smaller volume of fluid. Concentrating samples may prove useful when relatively small volumes are available for analysis. Additionally or alternatively, concentrating a sample may prove useful in introducing a sample from a macro-scale environment, such as from where a sample may have been collected, to a micro-scale or nano-scale environment, such as where analysis may be performed on the sample. In one embodiment, the device is configured to isolate, purify, and then process various types of samples, including, but not limited to DNA from microorganisms.

Figure 1:
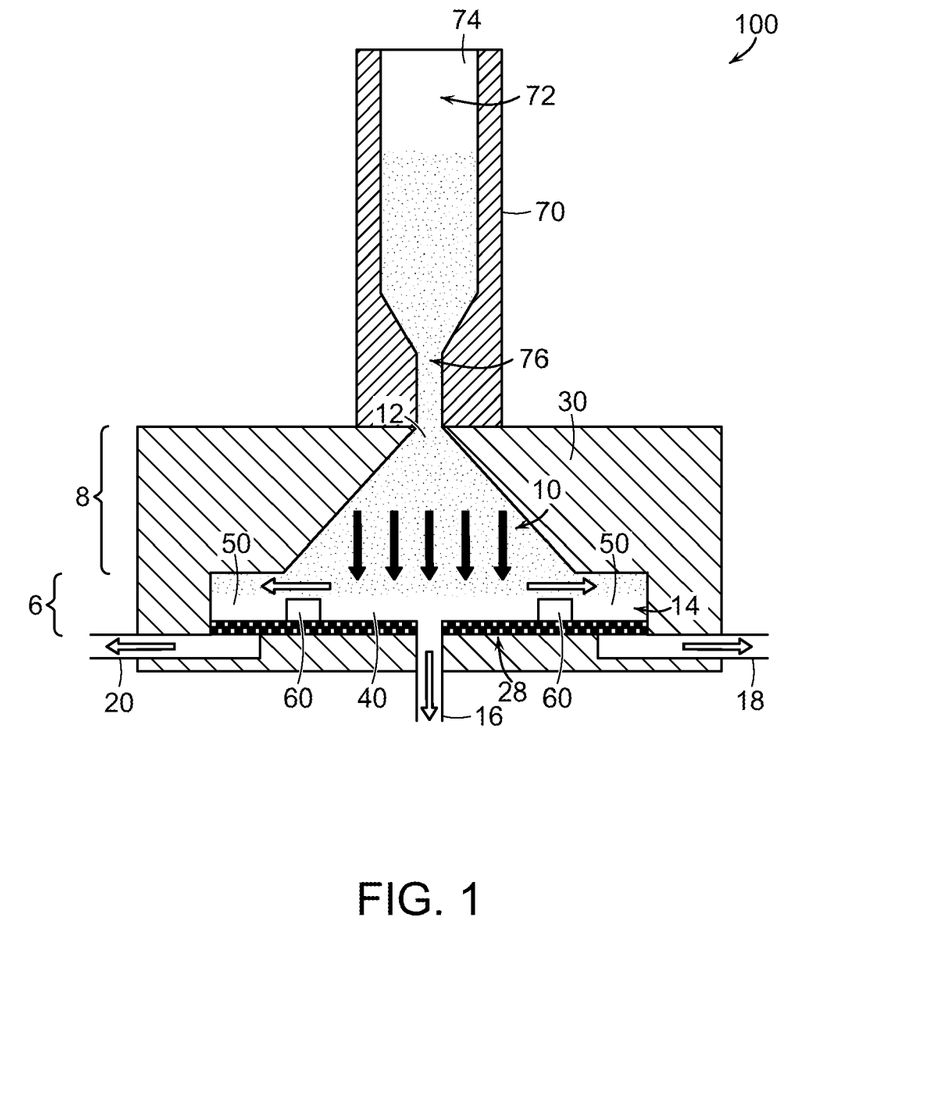
FIG. 1 is a schematic view of a device for preparing a sample according to one embodiment.

FIG. 1 illustrates one embodiment of a device 100 for preparing a fluid sample. The device includes a body 30 with a chamber 10 and an inlet 12. As shown, the inlet 12 may be centrally positioned at the top of the chamber 10 and is configured to move fluids into and/or out of the chamber 10. The device 100 also includes a porous membrane 14 that allows fluid but not the agents of interest to pass therethrough. A plurality of channels 16, 18, 20 are coupled to the bottom of the chamber. As illustrated, the inlet 12 is positioned on a first side of the membrane 14 and the plurality of channels 16, 18, 20 are positioned on a second side of the membrane, where the first side is opposite the second side. As set forth below, the channels 16 may be used to direct flow, typically introduced through the inlet 12, in different directions.

Embodiments of the chamber may be constructed with different configurations and dimensions, some examples of which are discussed herein. By way of example, the chamber 10 may provide a diffusive flow pathway between the inlet port 12 and the flow region, which, in many embodiments, may laterally spread the flow of fluid introduced through the inlet port to promote even distribution of agents about the porous membrane.

The chamber 10 may be shaped differently according to various embodiments. In one illustrative embodiment, the chamber 10 includes a diffuser portion 8 which is typically designed to smoothly widen or diffuse flow that enters the flow region from the inlet port without subjecting agents to excessive shear forces. As shown in FIG. 1, in one embodiment, the diffuser portion 8 of the chamber 10 is substantially frustoconical in shape. In one embodiment, the chamber 10 has a symmetric, truncated cone shape with substantially linear sides that form an angle of about 60 degrees with a line that extends along a central axis of the inlet port 12. It is to be appreciated, however, that the chamber may include walls that are angled differently, or that are gently curved instead of being linear, as aspects of the invention are not limited in this regard. In one embodiment, the chamber 10 has a symmetric, truncated cone shape with substantially linear sides that form an angle of about 45 degrees with a line that extends along a central axis of the inlet port 12. According to some embodiments, the chamber may include flat sides, appearing more like a truncated pyramid. Other embodiments may also include asymmetric chambers.

The inlet port 12 is typically positioned in the central portion of the chamber and is configured to direct a flow of fluid orthogonally toward the porous membrane 14 of the chamber 10. According to other embodiments, however, the inlet port 12 may be offset to one side of the chamber. Additionally or alternatively, the inlet port may direct fluid flow toward the membrane at an angle, instead of orthogonally. It is also to be appreciated that embodiments of the chamber may include a plurality of inlet ports positioned about the diffuser portion 8.

The chamber and/or inlet port, when described as being substantially opposed to the membrane 14, are understood to be positioned to direct fluid to impinge on a surface of the membrane. That is, at least a portion of the fluid flow is directed to intersect with the membrane 14.

The porous membrane 14 (also referred to herein as a substrate or a filter) is typically positioned to receive fluid flow that is introduced to the chamber from the inlet port 12, as shown in FIG. 1, such that a fluid sample passing therethrough may be received on the membrane 14. The membrane typically has a threshold size that relates to the porosity of the membrane and that describes the size or molecular weight of agents or other constituents that are prevented from passing therethrough. According to some embodiments, the membrane 14 has a threshold size that prevents the passage of cells, of genomic DNA, of proteins, and the like, although other threshold sizes are possible, as aspects of the invention are not limited in this respect. Some examples of membranes include ultrafiltration membranes. According to many embodiments, the membrane may be chosen such that it does not have an affinity for agents that may be processed in the chamber and thus does not prevent the agent from being removed from the chamber.

As set forth in more detail below, the membrane 14 may comprise a removable filter material that is held by a frit or support body 28, as shown in FIG. 1. Some operating protocols may utilize a membrane 14 with different threshold sizes, or that are constructed differently, and may benefit from being removable from the chamber. According to some embodiments, the membrane itself is relatively stiff, such that a support body may not be required.

In one embodiment, the chamber 10 may include a body section 6 that defines a wall of the chamber 10 that lies between the membrane 14 and the diffuser portion 8. As shown in FIG. 1, the body section 6 of the chamber 10 is substantially cylindrical in shape and extends for a relatively short distance between the diffuser portion 8 of the chamber 10 and the membrane 14. In other embodiments, the chamber 10 may be shaped differently, or the diffuser portion 8 of the chamber 10 may extend directly to the membrane 14, such that there is no body section 6 at all in the chamber 10.

A plurality of channels 16, 18, 20 are positioned adjacent the membrane 14, and as shown in FIG. 1, the channels 16, 18, 20 are positioned on a second side of the membrane 14 (i.e. on a side of the membrane opposite the inlet 12) and they each extend outwardly from the membrane 14. The particular embodiment illustrated in FIG. 1 includes a first channel 16 which extends outwardly from a central portion of the membrane 14, a second channel 18 which extends outwardly from a peripheral portion of the membrane 14, and a third channel which also extends outwardly from a peripheral portion of the membrane 14. In one illustrative embodiment, the first channel 16 extends outwardly from a central portion of the membrane, and the second and third channels 18, 20 extend outwardly from peripheral portions. As illustrated, the third channel 20 may be positioned on a peripheral portion of the membrane opposite the second channel 18.

The plurality of channels 16, 18, 20 are configured to be connected to an external pump or valve that controls the proportion of flow that passes though the channels. Any vacuum (or positive pressure) produced by the external pump, in turn, causes a vacuum (or pressure) in one or more selected channels 16, 18, 20 to move the fluid sample in the chamber. For example, if a vacuum is applied within the first channel 16, fluid within the chamber 10 will move into the first channel 16 and agents will collect along the central portion of the porous membrane 14. If a vacuum is applied within the second channel 18, fluid within the chamber 10 will move into the second channel 18 and agents may collect along the peripheral portion of the porous membrane 14, and similarly, if a vacuum is applied within the third channel 20, fluid within the chamber 10 will move into the third channel 20 and agents may collect along the peripheral portion of the porous membrane 14. As set forth in more detail below, in one embodiment, a vacuum may be applied within the first channel 16 to initially move the fluid sample and its agents toward the central portion of the membrane 14 (i.e. toward the first zone 40 of the membrane). Thereafter, a vacuum may be applied within the second channel 18 and/or the third channel 20 to move undesired agents and/or debris towards the peripheral portion of the membrane 14 (i.e. toward the second zone 50 of the membrane 14), thus isolating the desired agents on the central portion of the membrane 14. It is contemplated that a vacuum may also be applied within the first channel 16 at the same time that a vacuum is being applied within the second and third channels 18, 20. Flow may be reversed through the first channel 16 to move the desired agents on the central portion of the membrane out of the chamber 10. In one embodiment, when a vacuum is applied within the first channel 16, the fluid flows substantially normal or perpendicular to the membrane 14 such that the desired agents in the fluid sample press against the central zone of the membrane. When a vacuum is applied within the second and/or third channels 18, 20, the fluid may flow with a tangential component toward the peripheral portion of the membrane 14.

In one embodiment, the membrane 14 includes at least a first zone 40 and a second zone 50, where the first zone 40 is the central portion of the membrane 14 and the second zone is the peripheral portion of the membrane 14. In one embodiment, the second zone 50 substantially surrounds the first zone 40, and the second zone 50 may be substantially annular shaped. Other shapes are also contemplated, and in one embodiment, there may be a plurality of second zones 50 as the invention is not necessarily so limited. In one embodiment, the first zone is substantially circular shaped, although other shapes are also contemplated.

As shown in FIG. 1, in one embodiment, there is a barrier 60 which separates the first zone 40 of the membrane 14 from the second zone 50 of the membrane 14. The barrier 60 is configured to prevent movement of the sample through or within the membrane, to help to fluidly isolate the first zone 40 from the second zone 50. Thus, when a vacuum is drawn in the second zone 50 (i.e. with second and/or third channel 18, 20), the barrier 60 may be configured to prevent movement of the sample already positioned on the first zone 40 of the membrane 14.

It is recognized that the barrier 60 could be formed in a variety of different ways. For example, in one embodiment, the barrier 60 may be formed by a weld on the membrane material. The first and second zones 40, 50 of the membrane 14 may be made of one continuous membrane material with a weld formed therein to isolate the first zone 40 from the second zone 50. In another embodiment, the first and second zones 40, 50 may be formed of at least two membrane materials and another type of barrier 60, such as, but not limited to added layers of the membrane material, or other types of objects which physically separate the two zones 40, 50 may be employed.

Figure 6:
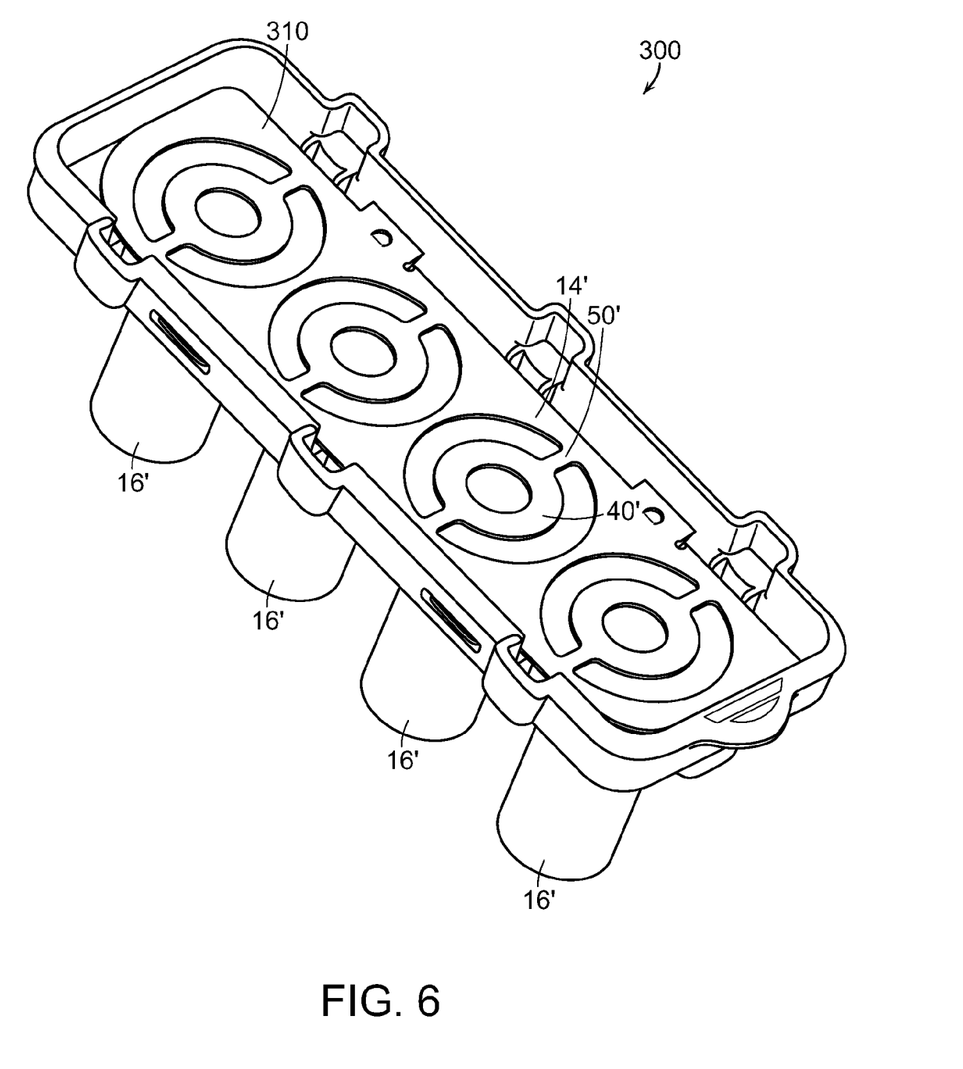
FIG. 6 is a perspective view of a portion of the device for preparing a sample according to one embodiment.

The size and shape of the membrane 14 and the barrier 60 may vary, but as shown in FIG. 6, in one embodiment, the membrane 14 includes a substantially annular shaped portion and the barrier is substantially annular in shape. It is also contemplated that the barrier 60 may be formed from an annular washer-like component. It is further contemplated that the barrier may be formed with a sealant.

As shown in FIG. 1, in one illustrative embodiment, the body 30 further includes a collar 70 extending upwardly from the chamber inlet 12. The collar 70 has a passageway 72 extending therethrough, and the passageway 72 has an inlet 74 configured to receive the fluid sample. In one illustrative embodiment, the collar inlet 74 is larger than the chamber inlet 12. Such a configuration enables the fluid sample to be more easily dispensed into the device 100, while also preventing disturbance to the reaction chamber 10. For example, the collar inlet 74 may be configured to receive a robotic probe which is configured to dispense a fluid sample into the device 100. In one illustrative embodiment, at least a portion of the collar passageway is frustoconical in shape as it narrows from the collar inlet 74 to the chamber inlet 12. However, other shapes are also contemplated as the present invention is not necessarily limited in this respect. In one embodiment, the collar passageway 72 is configured to act as a reservoir to hold a fluid, such as a buffer. As set forth below, the passageway 72 may be sized and shaped to hold a volume of the fluid sufficient to perform a particular function. For example, in one embodiment, the reservoir passageway 72 is configured to hold a volume that is at least approximately five times larger than the volume of the chamber 10. In one embodiment, the collar 70 includes a restriction 76 which separates the larger reservoir portion of the passageway 72 from the chamber inlet 12. This restriction 76 isolates the chamber 10 such that the reservoir fluid can be replaced without disturbing the chamber 10.

In one embodiment, the device 100 may also be equipped with features to regulate temperature in the chamber 10. According to one embodiment, a frit 28 that lies below and supports the membrane 14 is made of a thermally conductive material, like stainless steel, and may be heated or cooled by an external source, like a thermoelectric module, to regulate temperature. Additionally or alternately, fluid may pass through the chamber 10 to cool or heat the chamber. The chamber may also be equipped with other devices, like a radiant heater that heats fluid in the chamber through non-contact methods, or like an inline heater that heats fluids entering the chamber which, in turn, may help maintain uniform temperature conditions throughout the chamber volume.

Broadly speaking, the plurality of channels 16, 18, 20 are configured to receive fluid that has passed through the membrane from the flow region. As set forth below, the flow through the various channels 16, 18, 20 can be varied to control the movement of the fluid sample and the agents contained within the fluid sample. It is however to be appreciated that the channels 16, 18, may be used to accomplish other effects, such as heating and/or cooling of the flow region, as discussed herein.

Figure 2A:
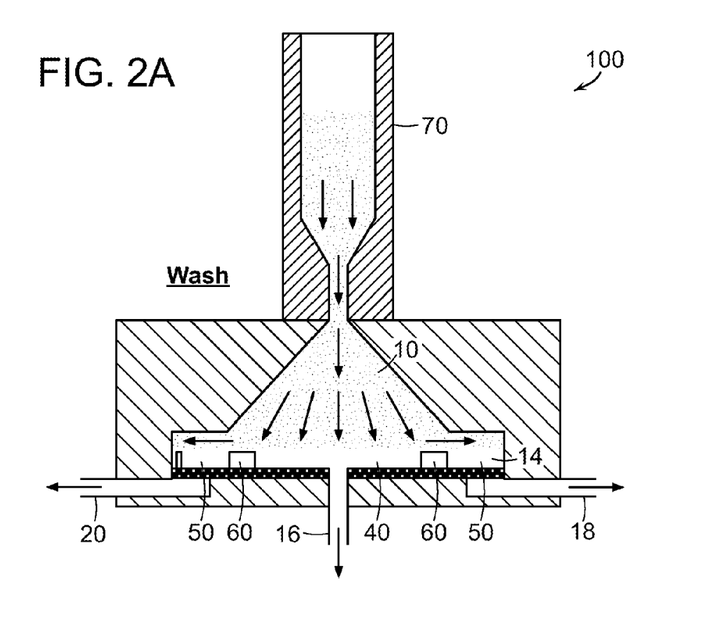
FIGS. 2A-2D are schematic views of a plurality of sample preparation steps that may be performed with the device illustrated in FIG. 1.

FIGS. 2A-2D illustrate a plurality of sample preparation steps that may be performed with the device 100 illustrated in FIG. 1. FIG. 2A illustrates a washing step in which a buffer is passed through the chamber 10 and that buffer passes through both the first and second zones 40, 50 of the membrane 14. In particular, as illustrated, a vacuum may be applied within the first channel 16, the second channel 18, and the third channel 20. The fluid buffer may already be positioned within the reservoir portion of the passageway 72.

Figure 2B:
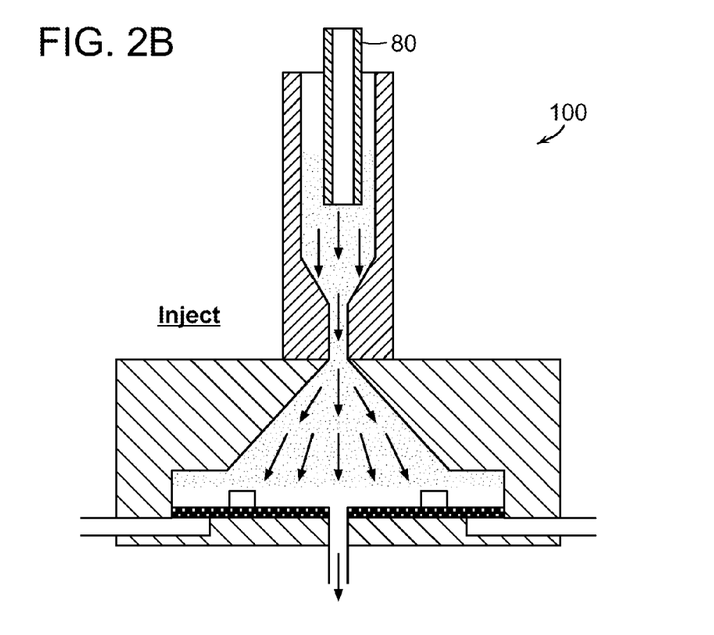

FIG. 2B illustrates an injecting step in which a fluid sample is injected into the device 100. In one illustrative embodiment, a robotic probe 80 is used to inject or dispense the fluid sample into the device 100. As illustrated, the device 100 may be filled with the buffer fluid when the fluid sample is being injected into the device 100. The type of fluid sample may vary, as the invention is not necessarily limited in this respect, but in one embodiment, the fluid sample contains DNA. In one embodiment, the sample may include a suspension of cells (such as but not limited to bacteria, yeast, molds, and/or mycoplasma). In one embodiment, the sample includes isolated nucleic acids varying in length from about 0.01 megabases to about 1 megabase in a fluid having a volume between about 10 µL to about 100 µL. In another embodiment, the sample includes isolated nucleic acids varying in length from about 0.01 megabases to about 0.1 megabases, and in another embodiment, the sample includes isolated nucleic acids varying in length from about 0.1 megabases to about 1 megabase.

In one embodiment, focused flow techniques may be employed during the injection step. In particular, the buffer fluid surrounding the probe 80 is utilized to focus the flow of the sample in the chamber 10. For example, a vacuum may be applied within the first channel 16 at a first flow rate. As mentioned above, this will cause the fluid in the chamber to move toward the central portion of the membrane 14. The fluid sample is injected into the device at a second flow rate. In one embodiment, the first flow rate is greater than the second flow rate, such that the buffer surrounding the probe 80 also moves toward the membrane. The flow rate of the buffer toward the membrane is approximately equal to the difference between the first flow rate and the second flow rate. This surrounding sheathed buffer flow may act to focus the flow of the sample toward the membrane 14 by constraining the sample towards the central portion of the membrane. In one particular embodiment, the first flow rate is approximately 200 microliters/minute, and the second flow rate is approximately 100 microliters/min, thus the resulting flow rate of the surrounding buffer is approximately 100 microliters/min. In another embodiment, the first flow rate is approximately 100 microliters/minute, and the second flow rate is approximately 50 microliters/min, thus the resulting flow rate of the surrounding buffer is approximately 50 microliters/min.

Figure 2C:
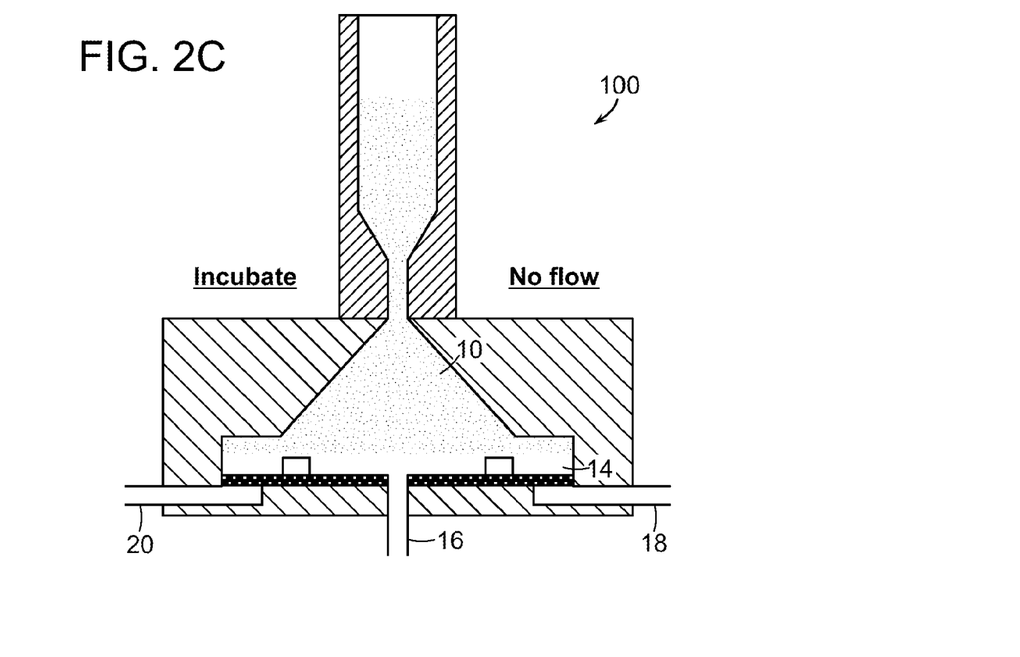

FIG. 2C illustrates an incubation step where there may be no fluid flow either into or out of the device 100. In one embodiment, the temperature of the chamber is increased using one of the above-described techniques. For example, the temperature of the chamber 10 may be increased to approximately 37° C.

Thereafter, another washing step may be performed as shown in FIG. 2A. In this washing step, the undesired cellular debris may be moved into the second peripheral zone of the membrane and the desired agents in the fluid sample, such as for example, the DNA sample, may be retained on the central portion of the membrane. As shown in FIG. 2A, a vacuum may be applied in the first central zone 40 of the membrane 14 to keep the bigger desired agents in the fluid sample on the first central zone 40 of the membrane 14. As also shown in FIG. 2A, a vacuum may also be applied in the peripheral second zone 50 of the membrane 14 to move smaller undesired components in the fluid sample away from the first central zone 40. As mentioned above, the barrier 60 may be configured to prevent the desired agents in the fluid sample from migrating from the first zone into the second zone. The device may be configured such that the larger particles/agents remain on the central portion of the membrane, whereas the smaller particles/agents move into the peripheral portion of the membrane.

The steps shown in FIGS. 2A-2C may be repeated one or more times. For example, a restriction enzyme may thereafter be injected into the chamber, as shown in FIG. 2B, and then the incubation step shown in FIG. 2C may be repeated. In one embodiment, a bacteria sample may be introduced into the chamber and the bacteria sample may remain on the membrane 14 while undergoing cell lysis, DNA extraction, DNA digestion, and/or DNA labeling.

Figure 2D:
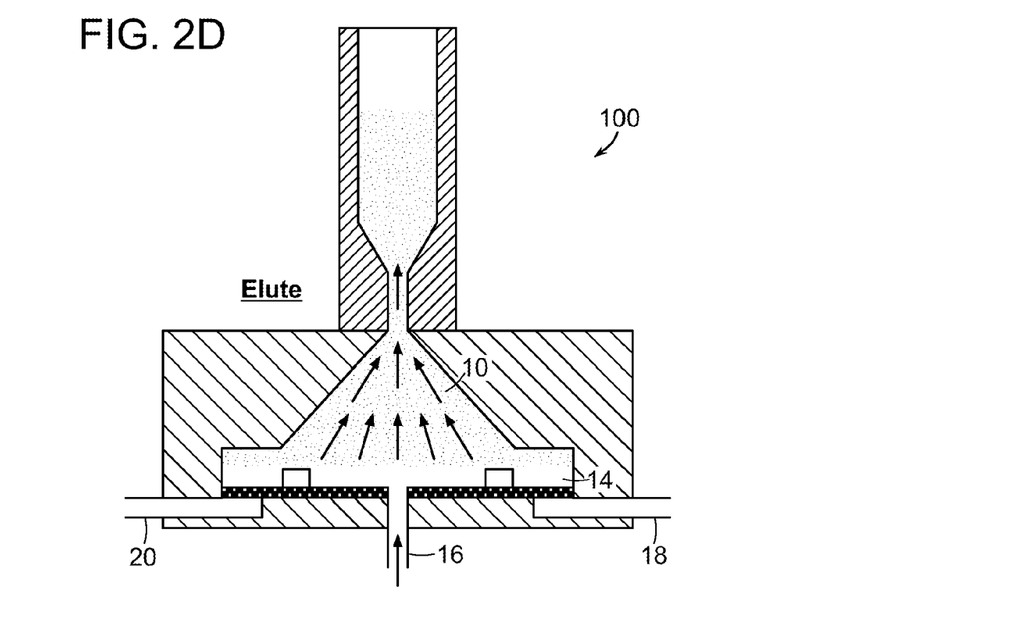

FIG. 2D illustrates the additional step of ejecting the desired sample from the device. As shown, this may be done by reversing the flow of fluid and applying a positive pressure through the first channel 16 such that the sample that has collected on the central portion of the membrane moves up through the chamber and out of the device. The barrier 60 may be configured to prevent the undesired debris, etc. in the second zone of the membrane from migrating over into the first central zone, thus the undesired debris may remain within the device 100. Once the desired sample has been removed from the device, the undesired debris, etc. that may have accumulated along the peripheral portion of the membrane may be removed from the device.

Figure 3:
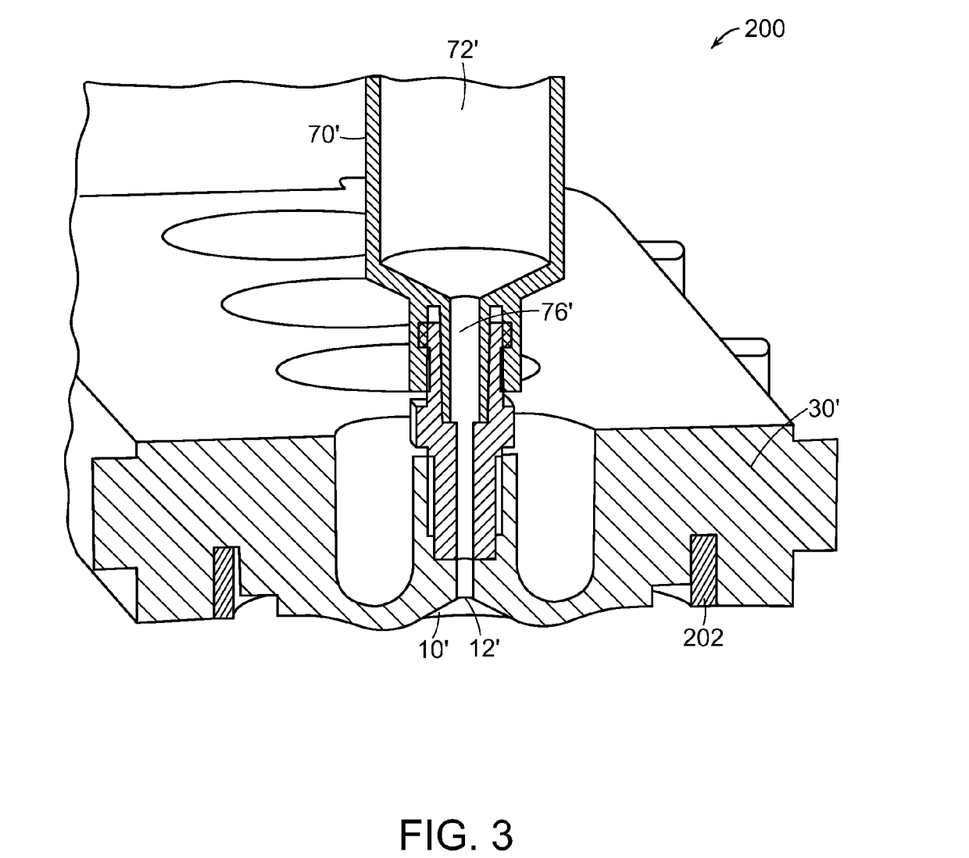
FIG. 3 is a perspective view of a portion of a device for preparing a sample according to one embodiment.
Figure 4:
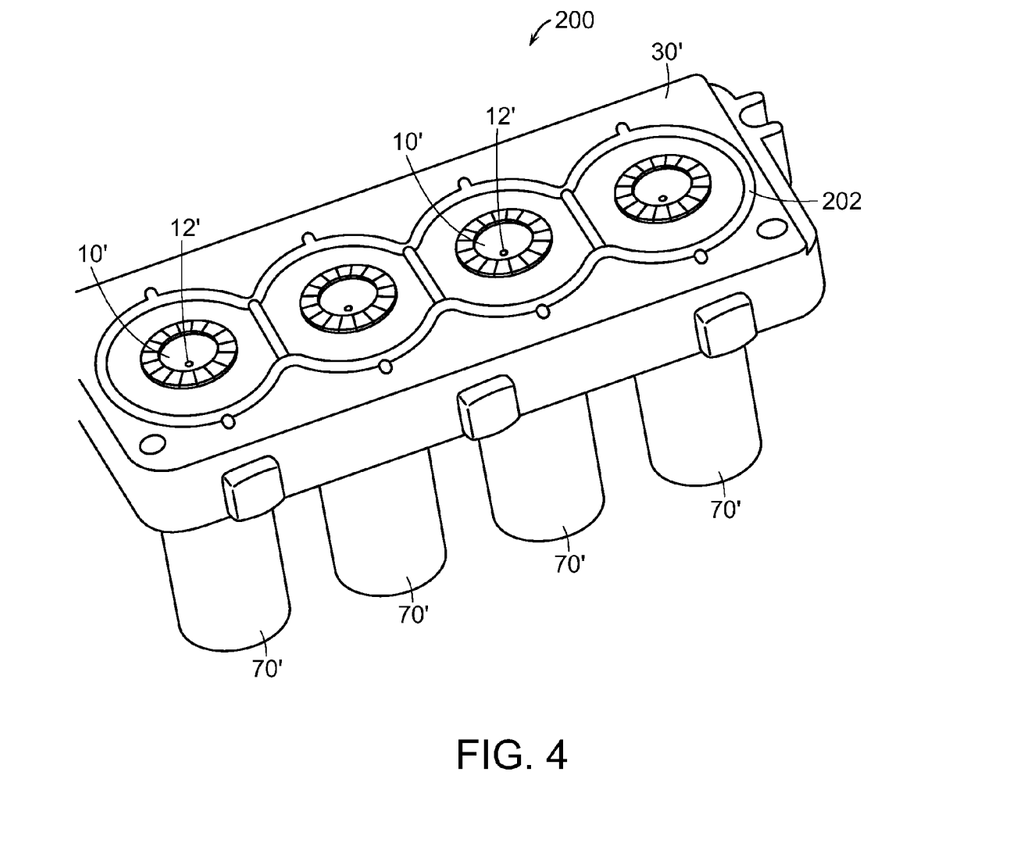
FIG. 4 is another perspective view of the first portion of the device shown in FIG. 3.
Figure 5:
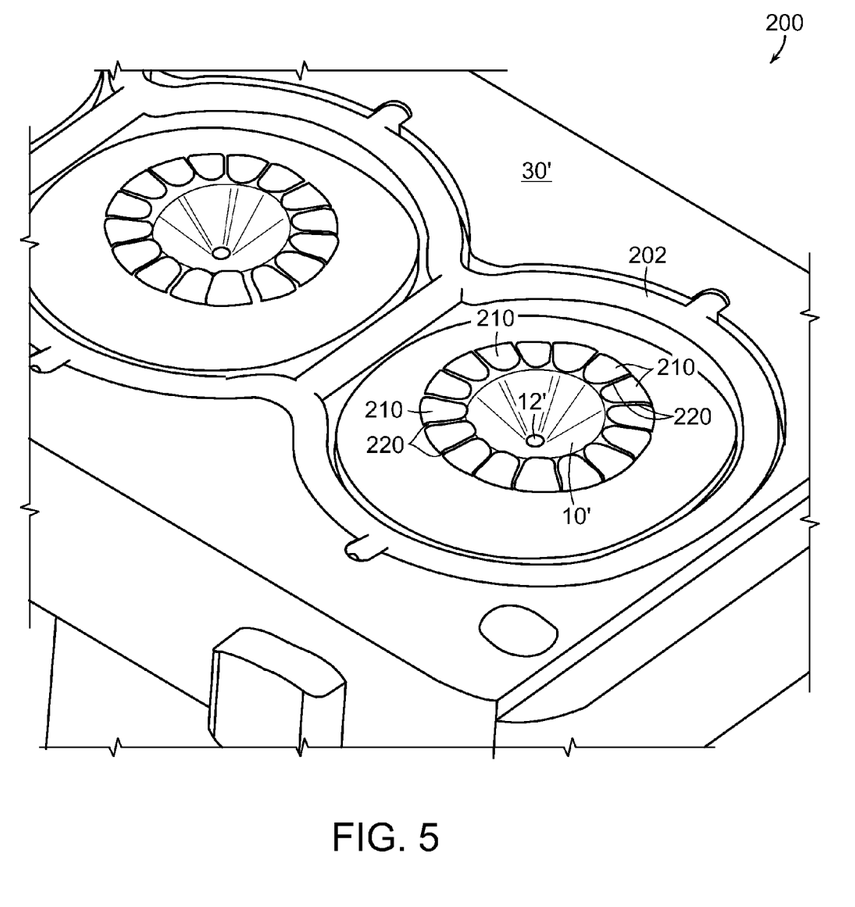
FIG. 5 is a detailed perspective view of the device shown in FIGS. 3 and 4.
Figure 7:
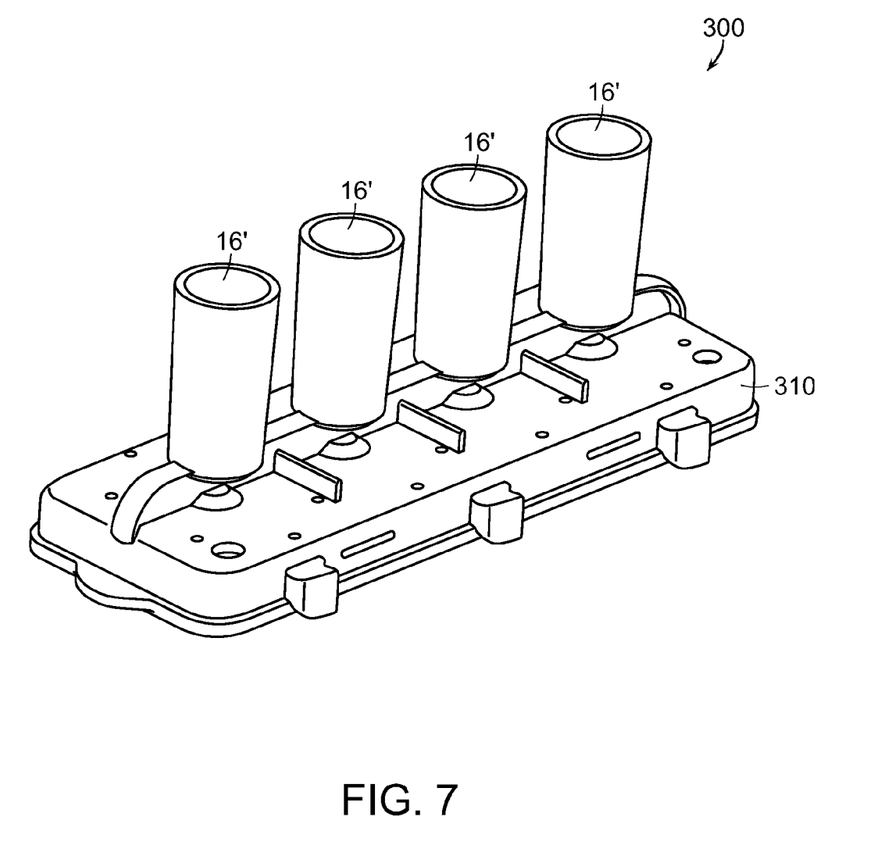
FIG. 7 is another perspective view of the portion of the device shown in FIG. 6.

FIGS. 3-5 illustrate one embodiment of a first portion 200 of a device for preparing a sample which is made from a solid starting material, and FIGS. 6 and 7 illustrates another embodiment of a first portion 300 of the device for preparing a sample which is injection molded. FIG. 6 illustrates a second portion 310 of the device for preparing a sample. The first portion 200, 300 and the second portions 310, when coupled together, may form a device which is substantially equivalent to the device 100 described above and shown in FIGS. 1-2. Accordingly, like components have been given identical reference numbers with a prime (') added.

As shown in FIGS. 3-5, the first portion 200 may include a body 30' with both the chamber 10' and the collar 70' formed within the body 30'. In this embodiment, there is a narrow restriction 76' that separates the chamber 10' from a reservoir portion of the collar passageway 72'. In one embodiment, the restriction 76' is at least three times the height of the chamber 10'. In another embodiment, the restriction 76' is at least five times the height of the chamber 10'.

As shown in FIGS. 6 and 7, the portion 300 may include a body 310 with the plurality of channels 16', 18', 20' formed within the body 310, and the membrane 14' may be configured to be coupled to the body 310 of the portion 300. This body 310 (which includes the channels 16', 18', 20') may be formed separately from the chamber body. One portion may be configured to be disposable and another portion may be configured to be reusable. In this particular illustrative embodiment, the first and second portions 300, 310 are configured to form a plurality of separate devices with chambers 10' for preparing a sample. In one embodiment, there are four isolated chambers 10' which are separated with an O-ring seal 202. Other configurations and numbers of chambers 10' are also contemplated, as the present invention is not so limited. For example, it is contemplated that a device with such a configuration may be used with a fluid dispensing device that includes a plurality of robotic probes 80.

As shown best in FIG. 5, the body 30' may include a plurality of downwardly extending feet 210 spaced apart around the perimeter of the chamber 10'. A plurality of passages 220 may be formed between the feet 210, and the passages 220 may be configured such that fluid can pass from the chamber 10' into the second zone 50 of the membrane 14'.

As shown in FIG. 6, in one illustrative embodiment, one sheet of membrane material may form a plurality of membranes 14' in adjacent chambers 10'. It is also contemplated that multiple membrane sheets may form the plurality of membranes.

As mentioned above, these first and second portions 300, 310 illustrated in FIGS. 3-7, when coupled together, may form a device which is substantially equivalent to the device 100 described above and shown in FIGS. 1-2. In one embodiment, the first portion 300 is configured as a disposable component. The first portion 300 may be a one-piece component in which the reservoir 70, restriction 76, chamber 10 and feet 210 are integrally formed, and for example, the first portion 200 may be molded. In another embodiment, the second portion 310 is configured as a disposable component.

Fluid flow may be controlled through the chamber during the various steps with different configurations of pumps and valves. According to some embodiments, flow is controlled by a first variable flow rate pump in fluid communication with the first channel 16 and by a second variable flow rate pump that is in fluid communication with the second and third channels 18, 20. It is to be appreciated, however, that other arrangements of pumps (either pressure or vacuum) and valves may be used to control flow through the chamber in various modes of operation, as aspects of the invention are not limited in this respect. Additionally, aspects of the invention are not limited to any one type of pump or valve.

Embodiments of the chamber may be operated by a controller that receives information for a particular operating protocol and, in turn, controls pumps and/or valves to run the system automatically to complete the protocol. The term 'automatically', as used herein, refers to a system that is capable of switching between modes of operation without the intervention of an operator, or to a system that is otherwise capable of altering operating conditions, such as flow rates or temperatures without manual operator intervention, such as by following a predefined operating protocol or by controlling the system to predetermined set points. The controller and operating protocol combination may be implemented in any of numerous ways. For example, in one embodiment, the controller and operating protocol combination may be implemented using hardware, software or a combination thereof. When implemented in software, the software code can be executed on any suitable processor or collection of processors, whether provided in a single computer or distributed among multiple computers. It should be appreciated that any component or collection of components that perform the functions described herein can be generically considered as one or more controllers that control the functions discussed herein. The one or more controllers can be implemented in numerous ways, such as with dedicated hardware, or with general purpose hardware (e.g., one or more processors) that is programmed using microcode or software to perform the functions recited above. The one or more controllers may be included in one or more host computers, one or more storage systems, or any other type of computer that may include one or more storage devices coupled to the one or more controllers.

In this respect, it should be appreciated that one implementation of the embodiments of the present invention comprises at least one computer-readable medium (e.g., a computer memory, a floppy disk, a compact disk, a tape, etc.) encoded with an operating protocol in the form of a computer program (i.e., a plurality of instructions), which, when executed by the controller, performs the herein-discussed functions of the embodiments of the present invention. The computer-readable medium can be transportable such that the treatment protocol stored thereon can be loaded onto any computer system resource to implement the aspects of the present invention discussed herein. In addition, it should be appreciated that the reference to an operating protocol or controller which, when executed, performs the herein-discussed functions, is not limited to an application program running on a host computer. Rather, the term operating protocol is used herein in a generic sense to reference any type of computer code (e.g., software or microcode) that can be employed to program a processor to implement the herein-discussed aspects of the present invention.

The device may also comprise one or more sensors that receive information from the chamber or channels used to connect the chamber to other portions of the device. Such sensors may receive information regarding pressure, temperature, flow rates, and the like, in any portion of the chamber or device. The device may also receive information for detectors that are used to analyze or detect the presence of an agent in a portion of the device.

It should be appreciated that various embodiments of the present invention may be formed with one or more of the above-described features. The above aspects and features of the invention may be employed in any suitable combination as the present invention is not limited in this respect. It should also be appreciated that the drawings illustrate various components and features which may be incorporated into various embodiments of the present invention. For simplification, some of the drawings may illustrate more than one optional feature or component. However, the present invention is not limited to the specific embodiments disclosed in the drawings. It should be recognized that the present invention encompasses embodiments which may include only a portion of the components illustrated in any one drawing figure, and/or may also encompass embodiments combining components illustrated in multiple different drawing figures.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. A device comprising:
a body having a chamber with an inlet;
a membrane positioned in the body, the membrane having a first side and a second side, wherein the inlet is positioned on the first side of the membrane;
a plurality of channels coupled to the bottom of the chamber, wherein the plurality of channels are positioned on the second side of the membrane, wherein each of the plurality of channels extends outwardly from the membrane, the plurality of channels including at least a first channel and a second channel, wherein the first channel extends outwardly from a central portion of the membrane, and wherein the second channel extends outwardly from a peripheral portion of the membrane,
wherein the membrane includes at least a first zone and a second zone, and there is a barrier which separates the first zone from the second zone, and
wherein the chamber body comprises a plurality of downwardly extending feet spaced around a perimeter of the chamber, with a plurality of passages formed between the feet configured such that fluid can pass from the chamber into the second zone of the membrane.

2. The device of claim 1, wherein the chamber is substantially frustoconical in shape.

3. The device of claim 1, wherein the body further comprises a collar extending upwardly from the chamber inlet, the collar having a passageway extending therethough, wherein the passageway has an inlet configured to receive a sample, wherein the passageway inlet is larger than the chamber inlet.

4. The device of claim 3, wherein at least a portion of the collar passageway is substantially frustoconical in shape as it narrows from the passageway inlet to the chamber inlet.

5. The device of claim 3, wherein the collar is integrally formed with the chamber.

6. The device of claim 1, wherein the membrane includes a substantially annular shaped portion and the barrier is substantially annular in shape.

7. The device of claim 1, wherein the barrier is formed of a weld on the membrane.

8. The device of claim 1, wherein the plurality of channels further comprises a third channel which extends outwardly from the peripheral portion of the membrane.

9. The device of claim 8, wherein the third channel is positioned on the peripheral portion of the membrane opposite the second channel.

10. The device of claim 1, wherein the plurality of channels are formed into a second body which is formed separately from the chamber body.

11. A method comprising:
introducing into the device of claim 1 a nucleic acid comprising sample;

manipulating the sample with one or more reagents; and
eluting nucleic acid from the device.

* * * * *